United States Patent [19]
Poon

[11] Patent Number: 5,394,342
[45] Date of Patent: Feb. 28, 1995

[54] LOG SCANNING

[75] Inventor: Joseph K. Poon, Burnaby, Canada

[73] Assignee: MacMillan Bloedel Limited, Vancouver

[21] Appl. No.: 23,433

[22] Filed: Feb. 26, 1993

[51] Int. Cl.⁶ .............................................. H04N 7/18
[52] U.S. Cl. ................................ 364/558; 364/474.09; 348/95; 382/8
[58] Field of Search ........... 364/507, 508, 558, 474.09; 356/372, 430, 431; 378/58; 348/552; 382/8

[56] References Cited

U.S. PATENT DOCUMENTS

| | | | |
|---|---|---|---|
| 4,879,752 | 11/1989 | Aune et al. | 382/1 |
| 5,023,805 | 6/1991 | Aune | 364/507 OR |
| 5,257,101 | 10/1993 | Lee | 364/468 X |

*Primary Examiner*—Emanuel T. Voeltz
*Assistant Examiner*—Kamini S. Shah
*Attorney, Agent, or Firm*—C. A. Rowley

[57] ABSTRACT

A log scanning system applies circumferentially spaced, traverse scans along the length of the log to provide a longitudinal density scan for each of the scans made. Each scan is made up of rows of density dependent pixels sensed by specific detector (scan line) and columns of density dependent pixels sensed by adjacent detectors arranged transversely of the log. The signals generated along each row to are filtered to produce a clean signal scan line and each clean scan line is processed to determine positive peaks. The positive peaks are plotted to form an image and adjacent peaks in adjacent rows and columns are joined to provide a spine image depicting spines of detected knots in each scan. Knot shapes are then defined by reprocessing each scan along the rows or scan lines to determine the knot boundaries on each side of each of the spine lines based on pixels displaying a selected minimum density and these shapes applied to the spine image to provide a reconstructed scan. The longitudinal axis of the log is determined and applied to the reconstructed scans to define the roots or inner ends of the knots. The reconstructed scans are then used to define the same knot in each of the reconstructed scans and then to generate a three-dimensional image of the log which may then be used by a sawing program to determine how the log should be sawed.

20 Claims, 5 Drawing Sheets

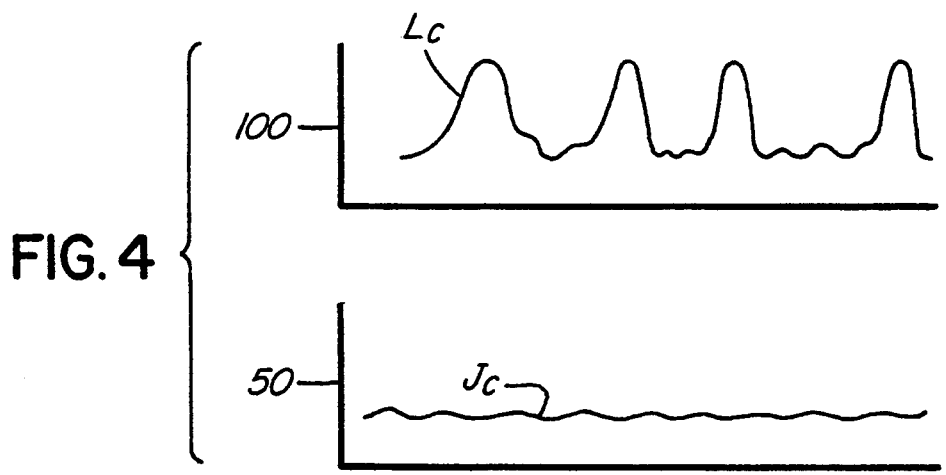
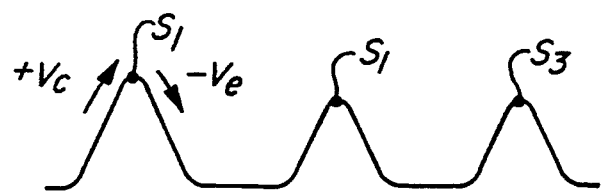
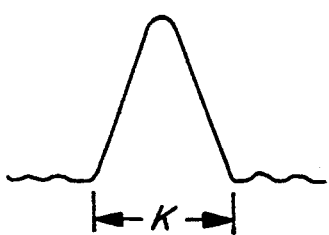
FIG. 4
FIG. 5
FIG. 6
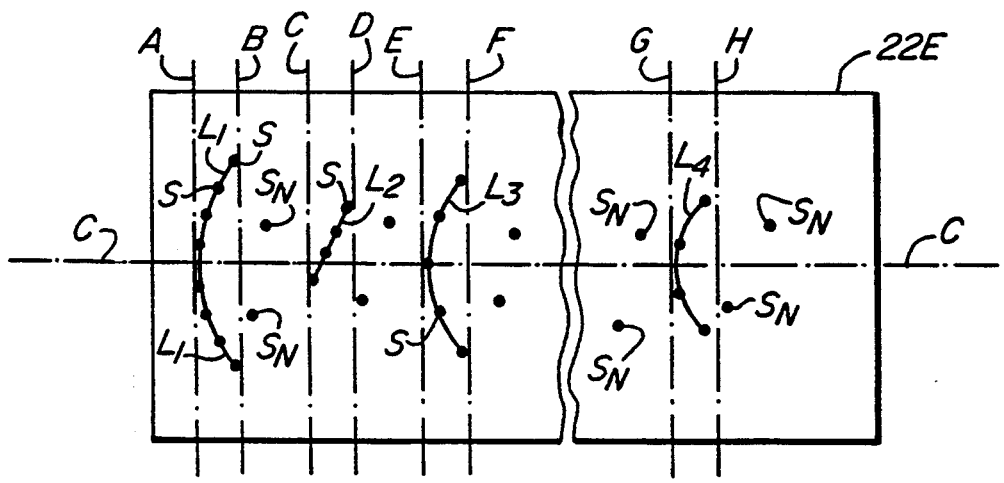
FIG. 7

LOG SCANNING

FIELD OF THE INVENTION

Present invention relates to log scanning, more particularly present invention relates to an improved method of reconstructing knots within a three-dimensional image of a log.

BACKGROUND OF THE INVENTION

The disclosure will be directed to scanning logs and development of the size, orientation and location of high density areas in a log which will normally represent knots although in some cases it may represent other intrusion such as nails, spikes, etc.

U.S. Pat. No. 5,023,805 issued Jun. 11, 1991 to Aune et al and incorporated herein by reference discloses a particular system for x-ray scanning of a log to define a position orientation and size of a knot in a log. This system has been implemented and is working satisfactory. However, it would be advantageous to increase the speed and accuracy of the knot detection and reconstruction for the sawing algorithm.

BRIEF DESCRIPTION OF THE PRESENT INVENTION

It is an object of the invention to provide an improved system for determining location and size of high density elements within a body such as a log.

Broadly the present invention relates to a system for analyzing a body to determine the position of elements of different density within said body comprising means to relatively move said body and a density scanning means in a direction along path of travel, said density scanning means including at least one source of electromagnetic energy located adjacent to and circumferentially spaced around said path positioned to pass electromagnetic energy through said body in a direction traversing said path as said body and said scanning means are relatively moved and sensor means for said source for sensing the amount of electromagnetic energy passing through said body form its said source and generate a scan, said sensor means composed of a plurality of discrete detectors arranged in circumferential side-by-side relationship relative to said path, each said detector being adapted to detect the amount of radiation received from its said source thereby to provide scan line of discrete values indicating the degree of attenuation of electromagnetic energy between each said discrete detector and its said source and define a scan line formed by a row of pixels in said scan extending in a direction representing the direction relative movement of said body and said detector, each said pixel providing a signal depicting density sensed by its said detectors, said circumferential side by side said detectors in said sensor means forming columns of said pixels in its said scan whereby each said scan generated by said sensor means is composed of lines and columns of pixels, filter means for filtering said density signals along each said scan line to provide cleaned signals, means to define positive peaks in each said cleaned signal along said scan lines, and means for plotting said peaks to form an image, means for joining for joining said peaks in adjacent of said scan lines and columns to form a spine image depicting spines of high density areas in each said scan.

Preferably said detector will comprise a plurality of said sources and corresponding said sensor means each of which generate a separate scan.

Preferably said system will further comprise means to define shapes of said high density elements by determining the areas represented by pixels above a selected threshold intensity along each said scan line on each side of said spines to provide a reconstructed scan, means to finding corresponding elements in each of said reconstructed scans and generating a three-dimensional image of said body with said elements arranged in their detected position and orientation in said three-dimensional image.

Preferably said elements will comprise knots and said body a log.

Preferably said means to filter will comprise a high pass filter means having a kernel length equivalent to at least the average number of pixels along a scan line representing the same knot.

Preferably said system will include means for defining longitudinal axis of said log thereby to define an inner end of each said knot.

Preferably said axis of a log will be determined by scanning each axial end of said log to find centre of the pit at each axial end of said log and interconnecting said centres at said axial ends of said log by a line spaced from the outer surface of said log by a calculated distance based on said centers and the axial spacing from one of said axial ends.

Preferably said system further comprise a sawing software, said sawing software providing a rotating decision, skewing decision, sawing decisions, based on the shape of and said axis of said log.

BRIEF DESCRIPTION OF THE DRAWINGS

Further features objects and advantages will be evident from the following detailed description of the preferred embodiments of the present invention taken in conjunction with the accompanying drawings in which:

FIG. 4 illustrates two typical scan line signals generated by spaced selected detectors.

FIG. 5 provides an indication of kernel length K compared with a signal as used to, define the high pass filter.

FIG. 6 shows a cleaned signal and the detection of the peaks representative of spine points.

FIG. 7 is a of spine image showing positive peaks plotted and selected peaks interconnected to define the spines of a knot.

DESCRIPTION OF THE PREFERRED EMBODIMENTS

Figure 1:
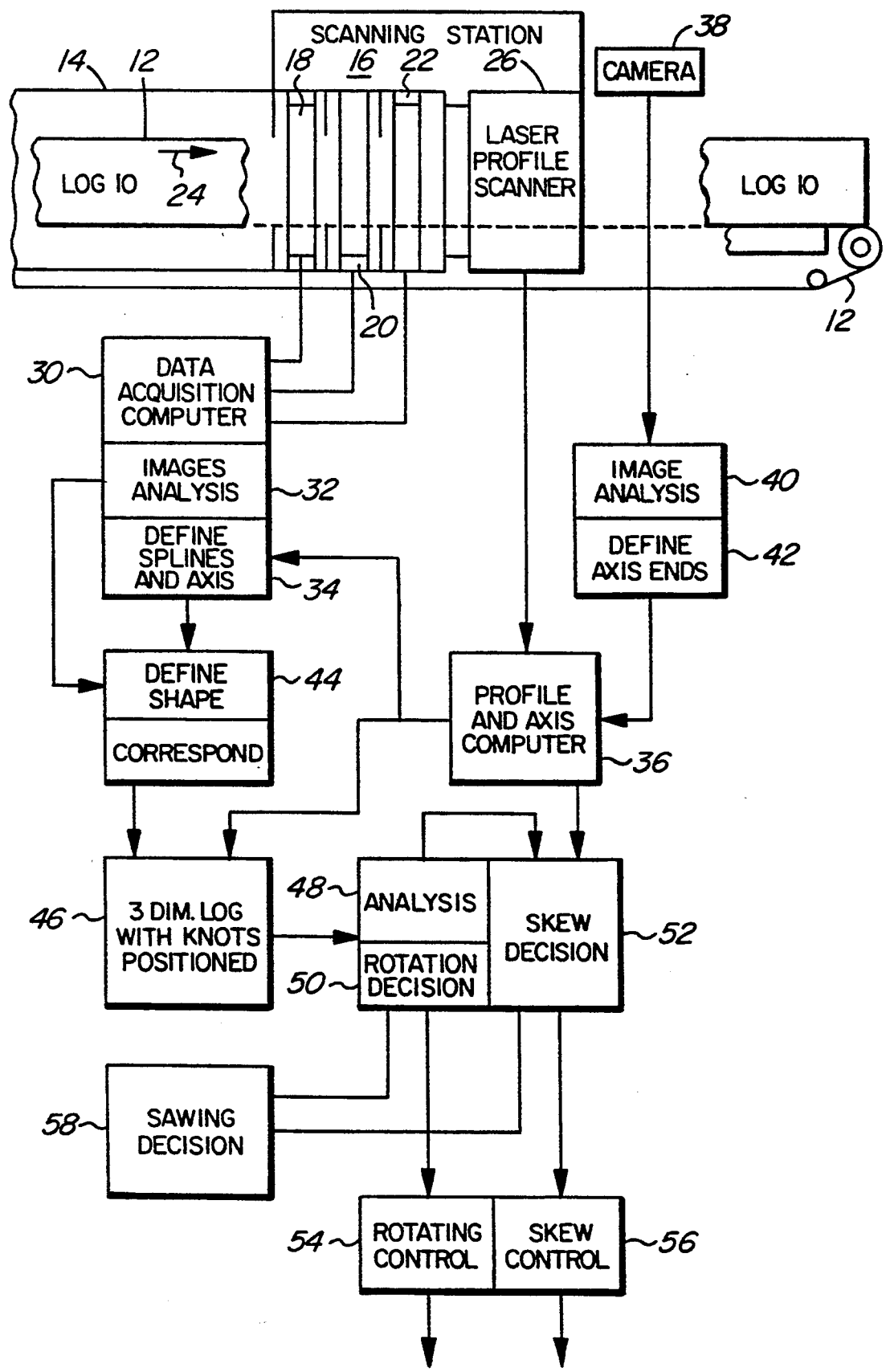
FIG. 1 is a schematic representation of a scanner system incorporating the present invention.

As shown in FIG. 1, a log 10 is carried on a conveyor 12 through an inlet housing 14 which preferably is designed to prevent the escape of radiation. The log 10 is carried on conveyors 12 through a scanning station 16 which includes preferably at least three scanners 18, 20 and 22 (two may be used but are not recommended as proper resolution is difficult with only two scanners) each passing electromagnetic energy substantially in a plane perpendicular to the direction of travel of the conveyor 12 so that the energy from each detector passes through the log in plane substantially perpendicular to the direction of log travel (i.e. radial to the log) as the log is carried by the conveyor 12 in the direction of the arrow 24 through the station 16. Generally, each of the scanners 18, 20 and 22 will pass electromagnetic energy, e.g. x-rays, through the log to determine the local density of the log, as will be described below.

Also included within the scanning station 16 is a laser profile scanner 26 which determines the outer dimensions of the log as it traverses the station 16 on a conveyor 12.

At least that portion of the conveyor 12 passing through the scanners 18, 20 and 22 preferably is a belt-type conveyor made of suitable material that does not interfere significantly with the operation of the scanners 18, 20 and 22. Some of the electromagnetic energy will be passed through the conveyor 12 to ensure the full cross section of the log is inspected.

Figure 2:
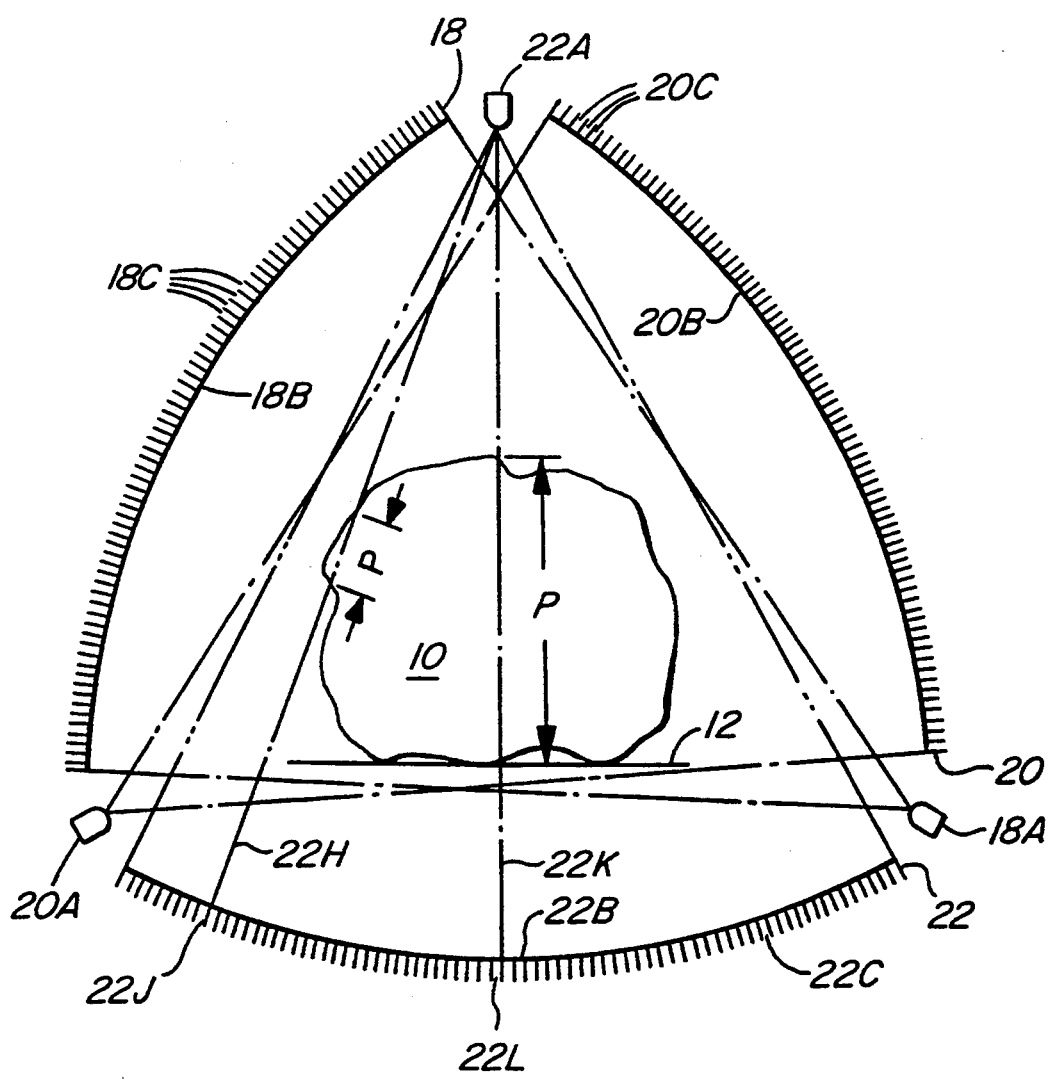
FIG. 2 is an end view of a typical scanner having three angularly spaced radiation sources and corresponding sensors.

The scanners 18, 20 and 22 are spaced along the length of the conveyor 12 however, for convenience in FIG. 2 all have been shown in essentially the same plane.

The scanner 18 includes a radiation source 18A and a sensor or detector array 18B positioned directly opposite the source 18A. Sensor 18B is composed of a plurality of discrete detectors 18C which preferably are approximately one-quarter inch in length measured in the axial direction of travel of the conveyor 12 and a similar width in the circumferential direction along the curvature of the detector 18B which preferably will be essentially on an arc the centre of which coincides with the source 18A.

The other scanners 20 and 22 include similar components each of which is indicated by the number of the scanner followed by the letter as described for scanner 18.

Figure 3:
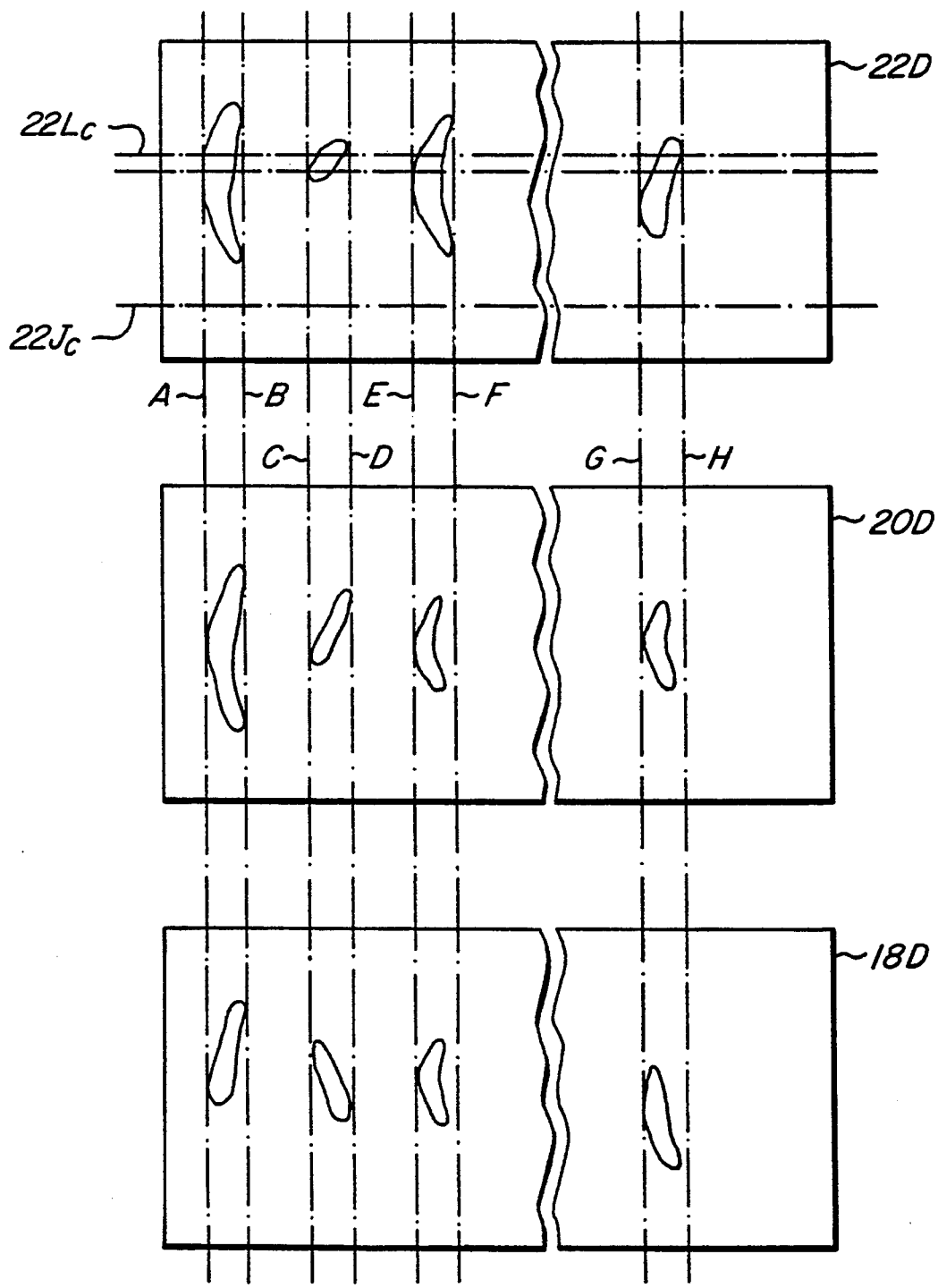
FIG. 3 illustrates typical scan generated by the sensors.
Figure 8:
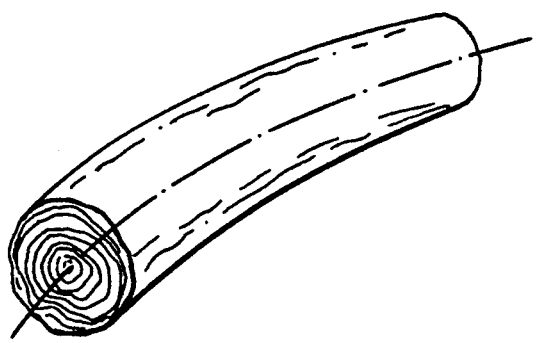
FIG. 8 schematically illustrates the how the axis of the log may be defined.

Each of the scanners 18, 20 and 22 is used to generate an axial 5 extending density scan based on the attenuation of the electromagnetic energy by the log as the energy passes from the sources 18A, 20A and 22A to their respective sensors 18B, 20B and 22B. Such a set of three axially extending density scans or projections are schematically illustrated in FIG. 3 for a selected length of a log (axially scans of the whole length of the log are generated as the log passes through the sensing station 16).

It will be noted that all of the projected scans are different, each being representative of density variations through the log at the different angles at which the sources project radiation through the log and as sensed by their respective detectors 18C, 20C and 22C as the log continually passes the scanners 18, 20 and 22. These longitudinally extending density scans are adjusted by calibration factors in the data acquisition computer section 30 (FIG. 1) and have been designated as scans 18D, 20D and 22D in FIG. 3 (the numeral corresponds with the sensor detecting the particular image). It will be apparent that each discrete axial length of one of the scans is matched (in the illustration aligned on the same plane) with a corresponding discrete axial length in the other scans (see the lines A, B, C, etc.).

The scans 18D, 20D and 22D acquired by the computer section 30 are then analyzed, for example, in a further computer section 32 by filtering (FIG. 4) along scan lines using a relatively long kernel (FIG. 5) as will be described in more detail below, based on the grey scale analysis, i.e. the scans 18D, 20D and 22D vary in brightness depending on the local densities of the log which indicates the degree of attenuation of the radiation passing through the log at each location.

It will be apparent that since the log is of non-uniform cross section, for example, may be substantially oval or circular in cross sectional shape, the length of the paths of travel of the electromagnetic energy rays through the log will be different in different areas of the log. Attention is again directed to FIG. 2. The ray 22H which is detected by the detector 22J passes through a thickness of the log 10 as indicated by the distance p whereas the ray 22K detected by the detector 22L passes through a thickness of log 10 indicated at P. It will be apparent that the attenuation of the ray 22H due to the body of the log perse is significantly less than the attenuation of the ray 22K simply because ray 22H passes through less wood than does the ray 22K and thus the signal produced by the detector 22J regardless of whether or not it traverses a defect in the log, will be significantly different than the signal generated by the ray 22K and will bias the scanning results accordingly. It is important that this portion of the signal as defined by body geometry be eliminated or rendered substantially insignificant so that the defects can be discerned.

The signals generated by each of the discrete detectors 18C, 20C and 22C for example the detector 22J and 22L are each processed individually along the length of the scan, i.e. in the direction parallel to the direction of movement of the log passed the source 22A. Each of these discrete detectors 22C defines a Channel or scan line in their respective scans 18D, 20D and 22D i.e. scan lines $22L_c$ and $22J_c$. It will be apparent that each of the scan lines for each of the detectors 18C, 20C and 22C is processed independently in a manner to distinguish discrete elements such as knots or rot from the remainder of the body of the log.

If the log being processed or the bodies being processed are all substantially symmetrical about a longitudinal axis, for example as may well be the case for logs produced from properly pruned trees which confine their knot locations in the pruned length, sufficient information may be available from processing a single axial scan and identifying the size and position of the knot core and swirls in the one scan (the other images will be quite similar) and use this information in determining a sawing solution, i.e. only a single scanner such as scanner 18 may be necessary.

In most logs, a single axial scan will not be sufficient and while two views may be used to determine the location of knots or other defects and position them in an image the accuracy of such a system is not as good as that obtained by using three separate sources and three sensors symetrically positioned around the log to provide three axial scans. Thus the remainder of this description will relate primarily to the use of three sources and three sensors and detecting and positioning defects within a body (log) based on three circumferentially spaced sensors as shown in FIGS. 2 and 3 generating three axial scans.

As above indicated, each of the detectors 18C, 20C and 22C generate signals and produce a scan line such as those indicated schematically at $22L_c$ and $22J_c$ in FIG. 3 in scan 22D. Each scan line obviously will provide individual data points or pixels along its line so that the pixels along the scan lines such as those illustrated $22L_c$ and $22J_c$ will form row of pixels. These pixels will combine pixels generated by other detectors in a sensor to form the scan which will thus consist of rows (generated by the same detector) and columns (generated by adjacent detectors) of data points or pixels in each of the generated longitudinal scans 18D, 20D and 22D.

The transverse lines such as lines A, B, C, D, E, F, G and H used to define the boundaries of different knots or high density elements as detected in each of the three scans also represent the arrangement in which the pixels data points of the various scan lines 22, 22Jc, etc. may be arranged in columns, each line such as the lines A, B, D, D, E, F, G and H could represent the columns generated by the adjacent detectors 18C in sensor 18B, the adjacent detectors 20C in the sensor 20B and the adjacent detectors 22C in the sensor 22B in each of the scans 18D, 20D and 22D.

A preferred system for identifying defects (knots) is to process the signal for each channel or scan line by successively kernelling the signal with a high-pass filter to leave only the defect information in the form of peaks.

In this manner, signals such as the signals illustrated in FIG. 4 may be processed even though the apparent thickness of the log at scan line $J_c$ is significantly different from (less than) the average thickness of the log at scan line $L_c$ so that the magnitude of the signal is significantly higher, i.e. the degree of attenuation is significantly higher when an inverse signal used.

By subjecting each of the signals to the high-pass filter having a kernel length K (shown in FIG. 5) which is at least equal to the base dimension number (i.e. the number of pixels) along the scan line for a knot (if the kernel is too small, it will not effectively define the peaks). Obviously the number of pixels determining this width of knot also depends on the frequency with which the scanners operate i.e. the number of pixels generated per unit length of relative movement between the log and the scanner and what is selected as a representative knot length in the scanning direction. The circumferential spacing and frequency of operation (number of columns per unit length of travel of the log) determine the degree of accuracy available from the equipment. It has been found that the kernel width of 32 representative of about ¼ inch (0.6 cm) along the log is effective for such scans. Thus most application the kernel width will be held at a constant K equal to 25 to 35 pixels for a system generating about 150 pixels per inch of travel of the log (32 pixels was selected for implementation of the system).

Each of the scan lines $22L_c$, $22J_c$, etc. will be processed using the high-pass filter as described to generate a clean signal such as the signal shown in FIG. 6 having discrete peaks indicated at $S_1$, $S_2$, $S_3$, etc. These peaks must be positive peaks, i.e. moving in the direction of the arrows in FIG. 6, the signal must convert from a positive to a negative slope so that only the high density peaks are marked.

These high density peaks are then plotted to form an image (one image for each scanner) and these images will be converted to spine images 18E, 20E and 22E (only image 22E is illustrated in FIG. 7).

As shown in FIG. 7, each of the peaks is plotted as indicated by the open circles some of which has been designated by the letter S and others by the designation $S_N$.

The next step in the process is to join adjacent peaks in the images to form the spine images such as the image 22E shown in FIG. 7 (similar images 18E and 20E will also be developed but have not been illustrated). The peaks to be connected are those immediately adjacent to one another, i.e. the peaks found in adjacent rows of scan lines and within a selected number of columns (generally within 2 columns) Thus lines such as those indicated at $L_1$, $L_2$, $L_3$, $L_4$ in FIG. 7 are formed by interconnecting the appropriate adjacent peaks S to define the spines of the knots, i.e. the line $L_1$ defines the spline of one knot or set of knots. Similarly, the spline $L_2$, $L_3$ and $L_4$ may define the spine of a knot or a plurality of interconnected knots. This operation is schematically illustrated in FIG. 1 by the block 34.

It will be apparent that some of the peaks such as those indicated at $S_N$ in FIG. 7 do not represent knots but are in fact signal noise and have been ignored in connecting of adjacent peaks to the to define the spine lines $L_1$, $L_2$, $L_3$, $L_4$, etc.

It is also important to determine the inner end of the knot or core of the knot so that it may be determined if more than one knot is represented by a spline $L_1$, $L_2$, etc. To define the core the centre line of the log is determined, preferably by using a laser scanner indicated at 26 to define the outer profile of the log (computed as indicated at 36) and by means of the camera 38 determining the centre of the pith at each axial end of the log 10.

The camera 38 is positioned in the sensing station and is adapted to produce an image of the leading end of the log as the log approaches and of the trailing end as the log is leaving. These images are then analyzed in image analyzer 40 and the ends of the longitudinal axis determined at 42 i.e. the location of the longitudinal axis or the pith is defined at opposite ends of the log 10. Todate, the simplest manner of analyzing the camera images has been to have the operator do the image analysis of the two end images and mark the centre of the pith in each image and deliver this information to the computer 36 which uses this information together with the computed profile of the log defines the position of the longitudinal axis of the log along the full length of the log.

The log axis need not be straight. Normally, the computer will define the centre line or the position of the log axis based on the defined centres in the two end images and by proportionally adjusting the position of the axis along the length of the log to maintain a similar position or proportional position of the centre (or axis) based on the spacing of the centre from the periphery of the log at each end and with change in distance along the axis from one end to the other of the log.

This longitudinal axis indicated as C in the spine image 22E of FIG. 7 is also applied as indicated by the block 34 in FIG. 1 to each of the spine images 22E (and 18E and 20E not shown) to define the core or centre line in each of the spine images 22E (18E and 20E) to define the core end of or divide the spine lines $L_1$, $L_2$, $L_3$, etc. into different knots i.e. the length of the each of the lines $L_1$, $L_2$, $L_3$, etc. on one side of the centre line C represents one knot and the adjoining length of the corresponding line $L_1$, $L_2$, $L_3$, etc. on opposite side of centre line C represents a second knot or several knots.

Figure 9:
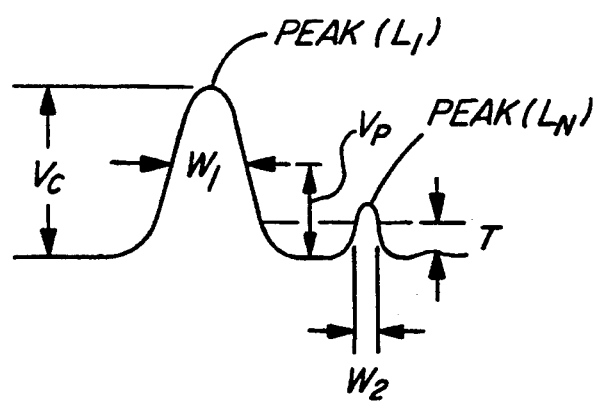
FIG. 9 schematically illustrates the reexamination of a signal on a scan line on opposite sides of a spine to define the shape of the knot for each of the scan lines in each of the scans.

It is also important to determine the size of each of the knot or knots represented by the spines $L_1$, $L_2$, etc. This is done as schematically indicated by the block 44 in FIG. 1 by reverting to the information represented in scans 18D, 20D and 22D of FIG. 3 and defining the width of the knot on either side of the spine L for each of the knot. As illustrated in FIG. 9, each of the scan lines (only one scan line $22L_c$ shown) is processed and the width of the knot relative to each of the spines $L_1$, $L_2$, etc. (as represented by the spine L in the portion of spine scan 22E represented in FIGS. 9 and 10) is determined by determining the widths $W_1$ and $W_2$ for each of the peaks in each of the scan lines $L_c$, $J_c$, etc. in each of the views 18D, 20D and 22D and applying these widths to the respective spine lines $L_1$, $L_2$, $L_3$, etc. in views 18E, 20E and 22E as illustrated for spine line L in FIG. 10.

Figure 10:
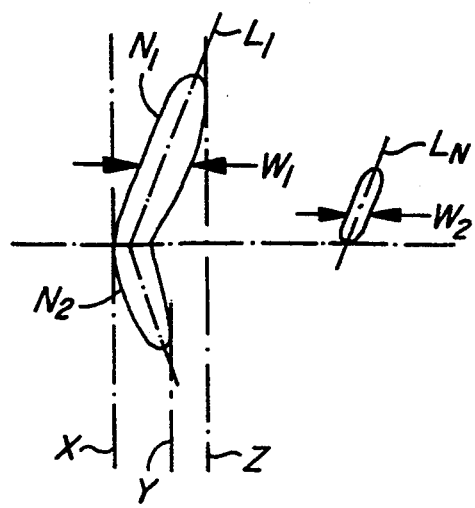
FIG. 10 is a partial illustration of a scan illustrating the knot found therein.

The widths $W_1$, $W_2$, as illustrated in FIGS. 9 and 10 are determined by retracing the signal of the scan line $L_c$, $J_c$, etc. On each side of a peak for a preselected distance and then determining the spacing between a left and right sides of the scan line at a preselected distance from the peak. For example, assuming the height of the peak above the base level signal is $V_p$ (see FIG. 9), i.e., the coordinant of the peak is $V_p$, starting from the peak ($L_1$) and searching left and right to a preselected level $V_t$ generally for the purposes of the present invention $V_t$ has been selected to be $V_t \leq V_p \times S$ where S is a preselected precentage (S=20% has been found satisfactory but a higher or lower percentage could be used). In some cases, $V_t$ will equal the threshold value T at which the basic signal is thresholded, i.e., when the peak is relatively small the amount it projects above the threshold value T will be very small. When the selected value $V_t$ is reached the spacing between the two points at level $V_t$ on the left and right sides of the peak are used to define the width of the knot as indicated by $W_1$ and $W_2$ in FIGS. 9 and 10.

The spine line L in spine scan 22E in FIG. 10 defines two knots $N_1$ and $N_2$ one on each side of the centre line C.

After the shape of the knots have been defined as above described and as schematically indicated at 44 in FIG. 1, it is then necessary to find corresponding knots in each of three spine scans 18E, 20E and 22E.

For simplicity bounding columns have been indicated at A, B, C, D, E, F and G for the various knots in FIG. 3. Normally, these projections would be along the column of pixels that define the extremities of the various knots. In practice these bounding columns A, B, C, etc. will be defined in the spine images 18E, 20E and 22E as shown in FIG. 7 but including the data on knot width as illustrated in FIG. 10. By finding the lateral extremities, i.e. the extremities of each knot section measure parallel to the scan lines such as line $22L_c$ and by projecting perpendicular to the scan lines $22L_c$, $J_c$ etc. as indicated at A, B, C, D, E, F, G etc. in FIGS. 3 and 7. Knots having similar extremities in a direction parallel to the log axis are found in each of the spine images 18E, 20E and 22E and it is assumed that knots having the same extremities in the three images represent essentially the same knot in these images. This information is then used to facilitate reconstruction of the knots in three-dimensional form. Thus, as t5 indicated in FIG. 10, images having corresponding extremities as indicated by the extremities X, Y and Z (X, Z representing the extremities of knot $N_1$ and X, Y representing of knot $N_2$) would be projected, as above described with respect to the boundaries and columns A, B, C, etc., onto the other images i.e. 18E, 20E (not shown) and corresponding knot images having similar extremities found in those images are deemed to be the same knot in each of the three images.

It is not always possible to predict with absolute certainty by using three images that a knot is in a specific location or orientation, i.e. depending on the extremities of the knot since other factors also apply, e.g. if there are three not two knots or if a number of knots are grouped into clusters the specific orientation of each knot may not be obtainable. Thus, if there is a possibility that a detected knot may have different orientations, it is preferred to reconstruct the three dimensional reconstruction with knots in each of the possible orientation or locations and assign a probability that this is the correct orientation. The probability factor assigned to knots reconstructed within a cluster is based on the number of known knots in a cluster of knots divided by the number of reconstructed knots as presented in the three dimensional configuration 100 (see FIG. 11).

Figure 11:
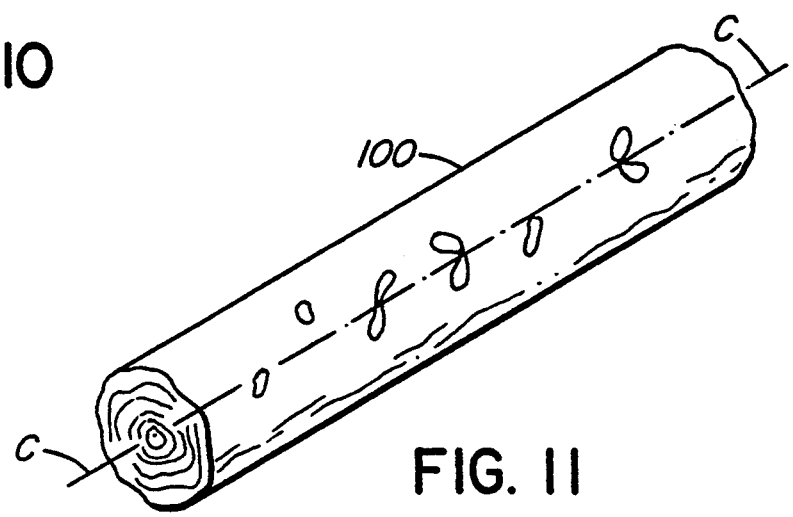
FIG. 11 is an isometric phantom view of the log illustrating the centre line and the axial position, orientation and size of the knots detected within the log.

The three dimensional reproduction is produced as indicated schematically by block 46 and is then fed to the computer (block 48) which analyses the three dimensional reconstruction 100 shown in FIG. 11 with the various reconstructed knots shown in axial spaced oriented positions and a rotation decision is made as indicated at 50 i.e. define which face of the log to be opened (opening face) and a skewing decision as indicated at 52 based on the profile determined at 36 and the axis C of the log. The rotation decision and skewing decisions are fed to the rotational control 54 and skewing control 5° which may be any suitable conventional rotational control and skewing control and they are also fed to the sawing decision computer 58 which makes a sawing decision as to how and where the cuts will be made relative to the opening face.

It will be apparent that an analysis of the log may include a bucking decision wherein the log is analysed based on the number of sawing decision on different length log sections and the log bucked into the selected lengths and then each length skewed and sawn based on the selected sawing and skewing decision for that length.

The above system provides a relatively rapid and accurate system for the determining the position orientation and size of knots within a log so that an improved yield or value from each log may be derived using appropriate sawing software programme.

Having described the invention, modifications will be evident to those skilled in the art without departing in the spirit of the invention as defined in the appended claims.

I claim:

1. A system for analyzing a body to determine the position of elements of different density within said body comprising means to relatively move said body and a density scanning means in a direction along path of travel, said density scanning means including at least one source of electromagnetic energy located adjacent to said path positioned to pass electromagnetic energy through said body in a direction traversing said path as said body and said scanning means are relatively moved and sensor means for said source for sensing the amount of electromagnetic energy passing through said body from said source and generate a scan, said sensor means being composed of a plurality of discrete detectors arranged in circumferential side-by-side relationship relative to said path, each said detector being adapted to detect the amount of radiation received from its respective said source thereby to provide scan line of discrete values indicating density as defined by the degree of attenuation of electromagnetic energy between each said discrete detector and its respective said source and define said scan line formed by a row of pixels extending in a direction representing the direction relative movement of said body and said detector, each said pixel providing a signal depicting density sensed by its respective said detector, said circumferential side by side said detectors in said sensor means forming columns of said pixels in its said scan whereby said scan generated by said sensor means is composed of lines and columns of pixels, filter means for filtering said density signals along each said scan line to provide cleaned signals, characterized by means to define positive peaks in said cleaned signal along said scan lines, and means for plotting said peaks to form an image, means for joining for joining said peaks in adjacent of said scan lines and columns to form a spine image depicting spines of high density areas in said scan.

2. A system as defined in claim 1 further comprising means to define shapes of said high density elements by determining the areas represented by pixels above a selected threshold intensity along each said scan line on each side of said spines to provide a reconstructed scan.

3. A system as defined in claim 2 wherein said elements comprise knots and said body a log.

4. A system as defined in claim 3 wherein said scanning means comprises a plurality of said sources and said sensor means to generate one of said means for each said source.

5. A system as defined in claim 3 wherein said system further includes means for defining a longitudinal axis of said log thereby to define an inner end of each said knot.

6. A system as defined in claim 5 wherein said means for determining said longitudinal axis of a log comprises means for scanning each axial end of said log to find centre of the pith at each axial end of said log and interconnecting said centers at said axial ends of said log by a line spaced from the outer surface of said axial log by a calculated distance based on the positions of said centers on said axial end and axial spacing from one of said axial ends.

7. A system as defined in claim 4 further comprise means to finding corresponding elements in each of said reconstructed scans and generating a three-dimensional image of said body with said elements arranged in their detected position and orientation in said three-dimensional image.

8. A system as defined in claim 5 further comprise means to finding corresponding elements in each of said reconstructed scans and generating a three-dimensional image of said body with said elements arranged in their detected position and orientation in said three-dimensional image.

9. A system as defined in claim 6 further comprise means to finding corresponding elements in each of said reconstructed scans and generating a three-dimensional image of said body with said elements arranged in their detected position and orientation in said three-dimensional image.

10. A system as defined in claim 8 wherein said system further comprises a sawing software, said sawing software providing a rotating decision, skewing decision, sawing decisions, based on the shape of and said axis of said log.

11. A system as defined in claim 1 wherein said means to filter comprises a high pass filter means having a kernel length equivalent to the least the average number of pixels along a scan line representing the same element.

12. A system as defined in claim 2 wherein said means to filter comprises a high pass filter means having a kernel length equivalent to the least the average number of pixels along a scan line representing the same element.

13. A system as defined in claim 3 wherein said means to filter comprises a high pass filter means having a kernel length equivalent to the least the average number of pixels along a scan line representing the same knot.

14. A system as defined in claim 4 wherein said means to filter comprises a high pass filter means having a kernel length equivalent to the least the average number of pixels along a scan line representing the same knot.

15. A system as defined in claim 5 wherein said means to filter comprises a high pass filter means having a kernel length equivalent to the least the average number of pixels along a scan line representing the same knot.

16. A system as defined in claim 6 wherein said means to filter comprises a high pass filter means having a kernel length equivalent to the least the average number of pixels along a scan line representing the same knot.

17. A system as defined in claim 7 wherein said means to filter comprises a high pass filter means having a kernel length equivalent to the least the average number of pixels along a scan line representing the same knot.

18. A system as defined in claim 8 wherein said means to filter comprises a high pass filter means having a kernel length equivalent to the least the average number of pixels along a scan line representing the same knot.

19. A system as defined in claim 9 wherein said means to filter comprises a high pass filter means having a kernel length equivalent to the least the average number of pixels along a scan line representing the same knot.

20. A system as defined in claim 10 wherein said means to filter comprises a high pass filter means having a kernel length equivalent to the least the average number of pixels along a scan line representing the same knot.

* * * * *